United States Patent
Suzuki et al.

(10) Patent No.: US 8,502,011 B2
(45) Date of Patent: Aug. 6, 2013

(54) ABSORBENT ARTICLE AND METHOD OF MANUFACTURING THE ABSORBENT ARTICLE

(75) Inventors: Nahomi Suzuki, Kanonji (JP); Koichi Yamaki, Kanonji (JP)

(73) Assignee: Unicharm Corporation, Ehime (JP)

( * ) Notice: Subject to any disclaimer, the term of this patent is extended or adjusted under 35 U.S.C. 154(b) by 335 days.

(21) Appl. No.: 13/000,669

(22) PCT Filed: Jun. 24, 2009

(86) PCT No.: PCT/JP2009/061479
§ 371 (c)(1),
(2), (4) Date: Mar. 1, 2011

(87) PCT Pub. No.: WO2009/157476
PCT Pub. Date: Dec. 30, 2009

(65) Prior Publication Data
US 2011/0184363 A1   Jul. 28, 2011

(30) Foreign Application Priority Data
Jun. 24, 2008 (JP) .............................. P2008-165153

(51) Int. Cl.
*A61F 13/15* (2006.01)

(52) U.S. Cl.
USPC ........... 604/364; 604/365; 604/367; 604/378; 604/385.101; 604/385.11

(58) Field of Classification Search
USPC .............. 604/364, 367, 378, 385.101, 385.11
See application file for complete search history.

(56) References Cited

U.S. PATENT DOCUMENTS

| | | | | |
|---|---|---|---|---|
| 3,131,693 A | * | 5/1964 | Gray et al. | 604/364 |
| 5,300,358 A | * | 4/1994 | Evers | 442/396 |
| 6,432,095 B1 | * | 8/2002 | Wada et al. | 604/385.01 |
| 6,433,245 B1 | * | 8/2002 | Bjorkquist et al. | 604/364 |
| 6,747,186 B2 | * | 6/2004 | Shimizu | 604/364 |

FOREIGN PATENT DOCUMENTS

| | | |
|---|---|---|
| JP | 2003530965 A | 10/2003 |
| JP | 2004298596 A | 10/2004 |
| JP | 2004344443 A | 12/2004 |
| JP | 2005130915 A | 5/2005 |
| JP | 2006075334 A | 3/2006 |
| WO | 0180911 A1 | 11/2001 |

OTHER PUBLICATIONS

International Search Report for PCT/JP2009061479 mailed Oct. 6, 2009.
Office Action corresponding to JP 2010-518037, dated Jul. 17, 2012.

* cited by examiner

*Primary Examiner* — Jacqueline F. Stephens
(74) *Attorney, Agent, or Firm* — Lowe Hauptman Ham & Berner, LLP (57) ABSTRACT

An absorbent article according to the present invention includes: a water-decomposable top sheet, a water-decomposable back sheet; and a water-decomposable absorber placed between the top sheet and the back sheet. The back sheet is formed of multiple sheet pieces each being smaller than a main body of the absorbent article, and each sheet piece at least partially overlapping adjacent one or more of the other sheet pieces. In addition, an adhesive is applied to each overlapping region where adjacent two of the sheet pieces overlap each other.

5 Claims, 8 Drawing Sheets

ABSORBENT ARTICLE AND METHOD OF MANUFACTURING THE ABSORBENT ARTICLE

TECHNICAL FIELD

The present invention relates to an absorbent article including: a water-decomposable top sheet, a water-decomposable back sheet; and a water-decomposable absorber placed between the top sheet and the back sheet, and to a method of manufacturing such an absorbent article.

BACKGROUND ART

Heretofore, as shown in Japanese Patent Literature #1, an absorbent article has been known in which a fastening piece for fastening the absorbent article to an undergarment is formed to protrude from both lateral sides of the main body.

When putting on the absorbent article, a wearer fastens the absorbent article to his/her undergarment by winding the fastening piece around the crotch of the undergarment.

In addition, in that absorbent article, the fastening piece is provided with a frangible portion for making the fastening piece easy to break, in order to facilitate removal of the absorbent article from the undergarment after use. Further, the absorbent article is formed by water-decomposable materials so that the absorbent article can be dispersible at a higher speed in a drainage pipe or in a septic tank.

However, the foregoing absorbent article relies solely on the fastening piece as means for fastening the absorbent article to an undergarment. Moreover, a region where the absorbent article is attached to the undergarment is located on a surface of the crotch of the undergarment to be in contact with wearer's clothes. Hence, the absorbent article has a problem that the absorbent article is liable to be separated away from the crotch as the wearer moves, and thus to be displaced from the undergarment.

In addition, since it is designed to be fastened by turning the fastening piece around the crotch of the undergarment, the foregoing absorbent article has a problem that the fastening piece might be brushed between the wearer' s groin and the crotch while the wearer is walking, which damages the frangible portion, and consequently makes the wearer feel uncomfortable.

CITATION LIST

Patent Literatures

[Patent Literature 1] Japanese Patent Application Publication No. 2004-298596

SUMMARY OF THE INVENTION

The present invention has therefore been made in consideration of the foregoing problems, and the present invention seeks to provide an absorbent article that has an improved fastening capability to an undergarment, and that is dispersible at a higher speed in a drainage pipe or in a septic tank, and to provide a method of manufacturing such an absorbent article.

A first aspect of the present invention is summarized as an absorbent article including: a water-decomposable top sheet; a water-decomposable back sheet; and a water-decomposable absorber placed between the top sheet and the back sheet. In addition, in the absorbent article, the back sheet is formed of multiple sheet pieces each being smaller in size than a main body of the absorbent article, and each sheet piece at least partially overlaps with adjacent one or more of the sheet pieces, and an adhesive is applied to each overlapping region where adjacent two of the sheet pieces overlap each other.

A second aspect of the present invention is summarized as a method of manufacturing an absorbent article that includes: a water-decomposable top sheet; a water-decomposable back sheet; and a water-decomposable absorber placed between the top sheet and the back sheet. Specifically, the method of manufacturing an absorbent article includes the steps of: continuously conveying multiple continua of back sheets on aback sheet line; placing the continua of back sheets to extend in a moving direction of the back sheet line so that each continuum of back sheets can at least partially overlap adjacent one or more of the continua of back sheets; and applying an adhesive to each overlapping region where adjacent two of the continua of back sheets overlap each other.

As has been described above, the present invention can provide an absorbent article that has an improved fastening capability to an undergarment, and that can be dispersed at a higher speed in a drainage pipe or in a septic tank, and can provide a method of manufacturing such an absorbent article.

DESCRIPTION OF THE EMBODIMENT (Structure of Absorbent Article According to a First Embodiment)

Figure 1:
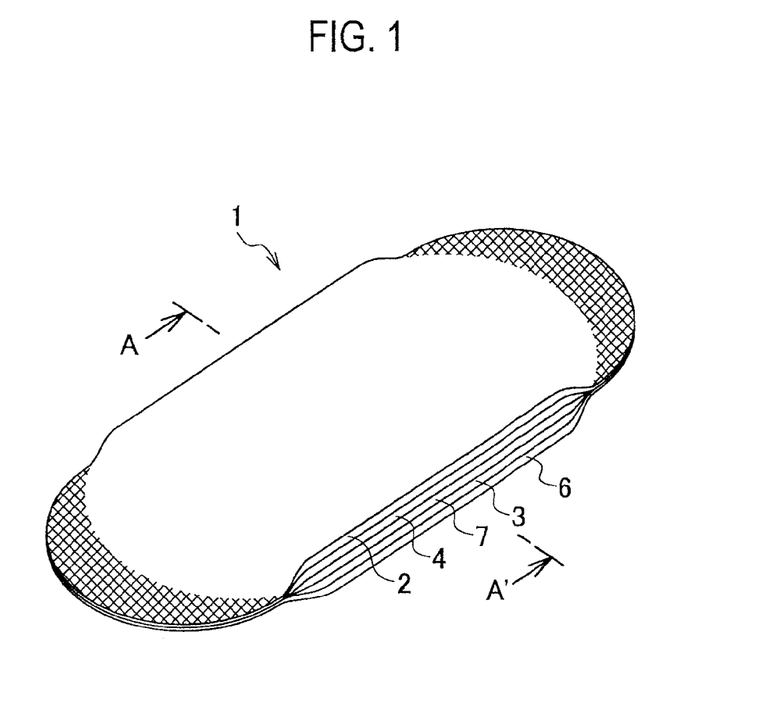
FIG. 1 is a perspective view showing an overall structure of an absorbent article 1 according to a first embodiment of the present invention.

Hereinafter, description will be given of a structure of an absorbent article according to a first embodiment of the present invention with reference to FIGS. 1 to 5. FIG. 1 is a perspective view of an absorbent article 1 according to this embodiment viewed from the top surface thereof (from a surface to be in contact with a wearer's skin).

Note that, in this embodiment, a party-liner is described as a representative example of the absorbent article 1 according to the present invention. However, the present invention is not limited to this, but is applicable to an incontinence pad, a diaper, a sanitary napkin or the like.

Figure 2:
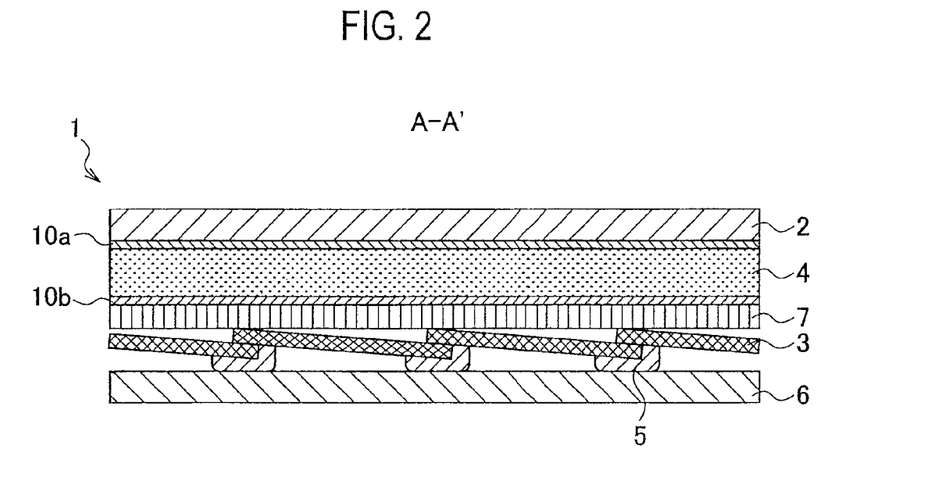
FIG. 2 is an A-A' cross-sectional view of the absorbent article 1 according to the first embodiment of the present invention.

As shown in FIG. 2, the absorbent article 1 has a water-decomposable top sheet 2, a water-decomposable back sheet 3 and a water-decomposable absorber 4 placed between the top sheet 2 and the back sheet 3.

A peeling paper 6 for maintaining adhesive properties of an adhesive 5 is provided on the back side of the absorbent article 1, or more specifically, on the back side (a surface to be in contact with the wearer's undergarment) of the back sheet 3. When putting on the absorbent article 1, the wearer exposes the adhesive 5 on the back side of the back sheet 3 by peeling off the peeling paper 6, and then attaches the absorbent article 1 to the crotch of his/her undergarment by bonding the absorbent article 1 thereto with the adhesive 5 thus exposed.

In addition, a waterproof paper 7 is provided between the absorber 4 and the back sheet 3, in this embodiment. Note that the waterproof paper 7 need not necessarily be provided. Accordingly, the waterproof paper 7 maybe appropriately provided in accordance with a performance required for the absorbent article 1.

The top sheet 2 and the absorber 4 are joined together with a water-soluble adhesive 10a, the absorber 4 and the waterproof paper 7 (the back sheet 3, instead, in the case where the waterproof paper 7 is not provided) are joined together with a water-soluble adhesive 10b.

The top sheet 2 is liquid permeable, hydrophilic and non-irritating to the wearer's skin. The top sheet 2 may be made solely of a water-decomposable non-woven fabric, or made of a composite material including a water-decomposable non-woven fabric.

While the wearer wears the absorbent article 1, the top sheet 2 might brush against the wearer's skin. This causes fibers of the top sheet 2 to fall out, and might eventually cause the top sheet 2 to wear out. To prevent this, the top sheet 2 may be alternatively made of a material based mainly on cellulose fibers, which are hydrophilic and, if contained in a sheet, increase the surface strength thereof.

Specifically, the top sheet 2 may be made of a wet spun-laced non-woven fabric having a fiber length in the 1 mm to 20 mm range formed as follows. A fiber blend containing 80 to 100 mass % hydrophilic fibers and 0 to 20 mass % fine-diameter hydrophobic fibers is dispersed at an area density not less than 20 g/m$^2$ but not more than 50 g/m$^2$. After that, these constituent fibers are entangled with one another by hydro-entanglement and then dried. Lastly, in this example, the obtained web is adjusted to have a thickness of not less than 0.3 mm but not more than 1.0 mm.

For example, the top sheet 2 may be made of a wet spun-laced non-woven fabric whose mass per unit area is adjusted to 40 g/m$^2$.

This non-woven fabric may contain unbeaten pulp (for example, 30 mass %), split microfibers (for example, 20 mass %), and rayon, preferably having a fineness of 1.1 dtex and preferably having a fiber length of 9 mm.

The absorber 4 is made of a liquid-retainable material such as water-decomposable non-woven fabric, water-decomposable air-laid pulp or water-decomposable paper.

For example, the absorber 4 may be made water-decomposable air-laid pulp. This pulp may have a mass per unit area which is adjusted to 70 g/m$^2$, and may contain pulp (for example, 80 mass %) and a water-decomposable binder (for example, 20 mass %).

The back sheet 3 is designed to be broken into pieces and dispersed by the flow and pressure of water in a flush toilet or a septic tank when flushed in a toilet.

The back sheet 3 is made of a material such as a water-decomposable non-woven fabric or a water-decomposable paper containing water-dispersible fibers. In the present embodiment, the back sheet 3 is divided into 4 pieces in the width direction of the absorbent article 1. Each of the divided sheet pieces of the back sheet 3 overlaps with each other at least partially. Further, an adhesive 5 is applied to the overlapping regions.

(Structure of Absorbent Article According to a Second Embodiment)

Figure 3:
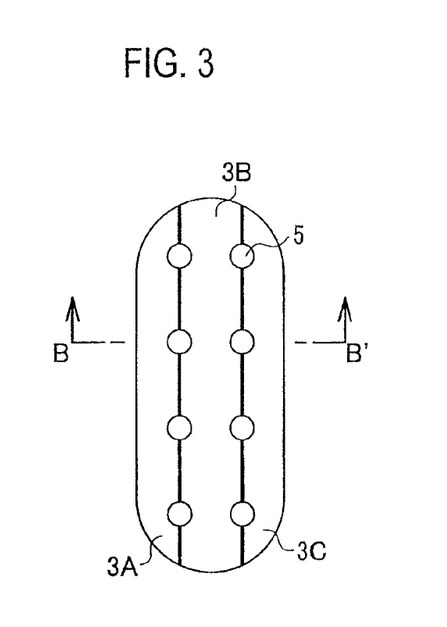
FIG. 3 is a plan view of a back sheet included in the absorbent article 1 according to a second embodiment of the present invention.

Hereinafter, description will be given of a structure of an absorbent article according to a second embodiment of the present invention. Hereinbelow, description will be given mainly on the portions different from the absorbent article 1 of the aforementioned first embodiment. Main differences on the absorbent article 1 between the first embodiment and the second embodiment is on the structure of the back sheet 3 and the regions to which the adhesive 5 are applied. As shown in FIG. 3, the back sheet 3 consists of multiple sheet pieces 3A to 3C each smaller than the main body of the absorbent article 1.

Figure 4:
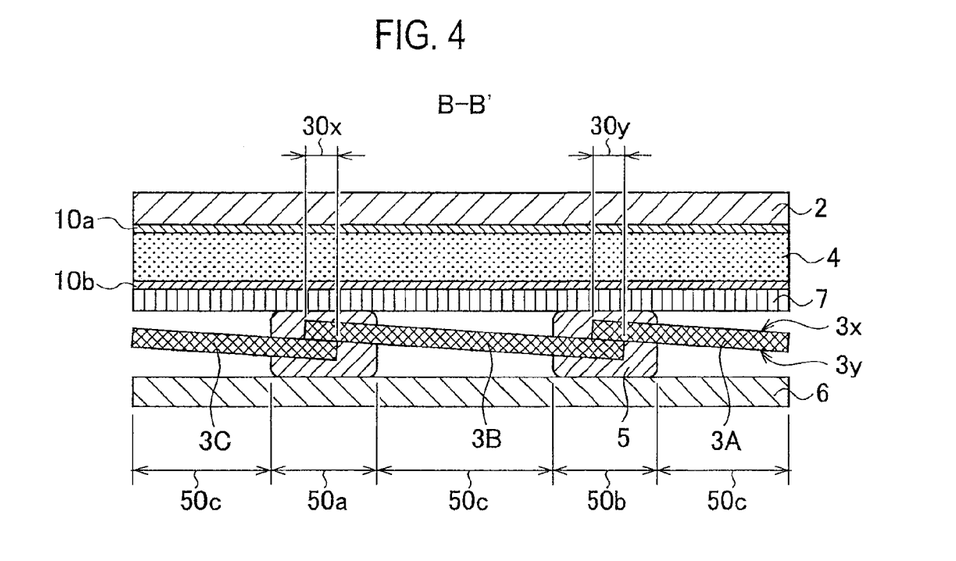
FIG. 4 is a B-B' cross-sectional view of the absorbent article 1 according to the second embodiment of the present invention.
Figure 5:
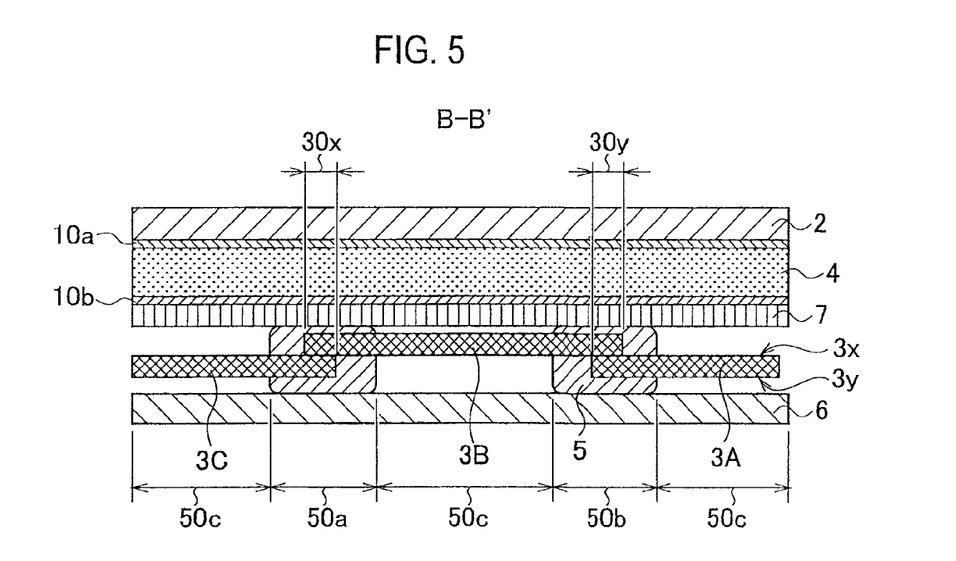
FIG. 5 is an alternative B-B' cross-sectional view of the absorbent article 1 according to the second embodiment of the present invention.

Each of the sheet pieces 3A to 3C at least partially overlaps adjacent one or more of the sheet pieces 3A to 3C. For example, the sheet pieces 3A and 3B may overlap each other, and the sheet pieces 3B and 3C may overlap each other, as shown in FIGS. 4 and 5. Note that FIGS. 4 and 5 are each a cross-sectional view of the absorbent article 1 taken along the B-B' line in FIG. 3. In the cross-sectional view shown in FIGS. 4 and 5, multiple sheet pieces 3A to 3C overlap in different manners. In the absorbent article 1 according to the present embodiment, any one of the overlapping shown in FIGS. 4 and 5 is applied.

The adhesive 5 is applied to each overlapping region where adjacent two of the sheet pieces 3A to 3C overlap each other. For example, as shown in FIGS. 4 and 5, the adhesive 5 is applied to an overlapping region 30x where the sheet pieces 3A and 3B overlap each other, as well as to an overlapping region 30y where the sheet pieces 3B and 3C overlap each other.

In the example shown in FIGS. 3 to 5, the overlapping regions 30x and 30y are arranged to extend in the longitudinal direction of the absorbent article 1. The overlapping regions 30x and 30y are portions in which a part of multiple sheet pieces overlapping with the adjacent sheet piece each other. It is preferable that the peripheral portions of each sheet pieces overlaps so as to form the overlapping portions 30x and 30y, as shown in FIGS. 4 and 5.

Specifically, it is preferable that at least 5% of the planar area of the sheet piece overlaps with the adjacent sheet piece so as to form the overlapping portions 30x and 30y. It is more preferable that at least 10% of the planar area of the sheet piece overlaps with the adjacent sheet piece. Further, it is preferable that the overlapping portions 30x and 30y be set not more than 50% of the planar area of the sheet piece. It is more preferably that the overlapping portions 30x and 30y be set not more than 25% of the planar area of the sheet piece. Note that, a part of the sheet pieces need not necessarily overlap to form the overlapping portions 30x and 30y. Alternatively, for example, whole portion of the certain sheet piece may be formed to overlap with a part of other sheet piece. In other words, preferable range of the overlapping portions 30x and 30y is 10% to 25% of the planar area of the sheet piece.

In the sheet pieces 3A to 3C, regions not coated with the adhesive 5 serve as entrances through which water enters the inside of the absorbent article 1 when the absorbent article 1 is disposed of in a flush toilet after use, and thus put into water.

In addition, each of the sheet pieces 3A to 3C may be not more than 50 mm in length and width, or preferably be not more than 30 mm in length and width, so as not to entangle around a diffuser in a septic tank.

Having a size small enough to readily sink in a settlement tank in a septic tank as described above, the sheet pieces 3A to 3C may be made of a non-water-decomposable material. In other words, there is no problem even if the sheet pieces 3A to 3C are made of a non-water-decomposable material, since the sheet pieces 3A to 3C can flow to a settlement tank and sink therein, and will be collected when the settlement tank is cleaned.

The sheet pieces 3A to 3C may be contiguously connected, or more specifically, the sheet pieces 3A to 3C may be caused to partially overlap and the adhesive 5 may be applied to the overlapping regions, by the following method for example. For example, three sheet pieces 3A to 3C in total each being approximately 100 mm in length and approximately 20 mm in width are arranged in one line in the longitudinal direction and three lines in the width direction so as to partially overlap. Then, the sheet pieces 3A to 3C are joined together and the adhesive 5 in a pattern of circles is applied to the overlapping portions.

In addition, the back sheet 3 (sheet pieces 3A to 3C) is made of a water-decomposable non-woven fabric or a water-decomposable paper, for example.

Specifically, the back sheet 3 (the sheet pieces 3A to 3C) may be made of a material including: (1) a water-decomposable non-woven fabric formed by entangling water-dispersible fibers each having a relatively small fiber length with one another by the flow of water; (2) a water-decomposable paper shaped into a sheet, which is formed by water-dispersible fibers, such as pulp and rayon, blended with a water-soluble binder for binding the fibers; (3) a water-decomposable paper formed by shaping pulp into a sheet by utilizing hydrogen bonding among the constituent pulp fibers; (4) a water-decomposable paper formed by entangling water-dispersible fibers with one another and then by shaping the entangled fibers into a sheet; or the like. In addition, in order to make the back sheet 3 impermeable to liquid, the surface thereof may be treated with a water repellant finish by applying a biodegradable resin, such as polylactate or polyvinyl alcohol, to the surface.

Specifically, the back sheet 3 (the sheet pieces 3A to 3C) may be made of a wet spunlaced non-woven fabric, which may have a fiber length in the 1 mm to 20 mm range formed as follows. Fiber blend containing pulp fibers (for example, 30 to 70 mass %) and rayon fibers (for example, 30 to 70 mass %) is dispersed at an area density in the 20 g/m² to 50 g/m² range. After that, these constituent fibers are entangled with one another by hydro-entanglement and then dried. Lastly, the obtained web is adjusted to have a thickness which is preferably in the range of 0.1 mm to 1.0 mm range.

For example, the back sheet 3 (the sheet pieces 3A to 3C) is made of a wet spunlaced non-woven fabric whose mass per unit area is adjusted to 40 g/m². This non-woven fabric may contain beaten pulp (for example, 30%), unbeaten pulp (for example, 20%), and rayon preferably having a fineness of 1.1 dtex and a fiber length of 7 mm.

Note that, as shown in FIGS. 4 and 5, in each overlapping regions 30x and 30y where adjacent two of the sheet pieces 3A to 3C overlap each other, the adhesive 5 is applied so as to be exposed to both the side of the waterproof paper 7 (that is, the absorber 4 side) and the side of the peeling paper 6. This allows a wearer to bond the absorbent article 1 to the undergarment with the adhesive 5 used for joining the sheet pieces 3A to 3C when he/she attaches the absorbent article 1 to his/her undergarment.

In addition, the adhesive 5 is discontinuously applied to each of the overlapping regions 30x and 30y. Specifically, the adhesive 5 is applied in a pattern, which is discontinuously arranged at certain intervals; for example, a pattern in which repeated circles as shown in FIG. 3 or repeated rectangles are arranged at certain intervals.

In other words, the adhesive 5 is applied to multiple areas spaced apart from one another in the back sheet 3 so as to join the sheet piece 3A to 3C together and to be exposed on the surface of the back sheet 3 to be in contact with a wearer's undergarment.

The adhesive 5 may be applied in a pattern as described above by a method such as slot coating, spray coating, porous coating, using a roll coater, and gravure coating. Among these, a coating method using a roll coater is preferable, since it enables a pattern design of adhesive having certain intervals.

A coating amount of the adhesive 5 for each pattern is preferably within the 10 g/m² to 250 g/m² range, and is most preferably within the 50 g/m² to 150 g/m² range.

If the coating amount of the adhesive 5 for each pattern is not more than 50 g/m², adhesion strength between the absorbent article 1 and a wearer's undergarment tends to be too reduced. Because, most of the adhesive 5 is absorbed by and retained within the back sheet 3 (sheet pieces 3A to 3C) in this case, and thus only a small amount of the adhesive 5 is exposed on the surface of the back sheet 3 to be in contact with the undergarment.

On the other hand, if the coating amount of the adhesive 5 for each pattern is not less than 150 g/m², adhesion strength between the absorbent article 1 and a wearer s undergarment tends to be too increased. Because, a large amount of the adhesive 5 is left unabsorbed by and thus not retained within the back sheet 3 (sheet pieces 3A to 3C), and consequently exposed on the surface of the back sheet 3 to be in contact with the undergarment. The too-increased adhesion strength is likely to cause so-called material breakage, a phenomenon where the back sheet 3 and the absorber 4 are broken and thus partly left unpeeled from the undergarment when the absorbent article 1 is peeled off from the undergarment.

Each shape in the pattern of the adhesive 5 is smaller than the sheet pieces 3A to 3C, and should preferably have a size in the order of 1 mm to 10 mm. The shape in the pattern of the adhesive 5 may be a circle having a diameter from 1 mm to 10 mm, a quadrangle whose side lengths are from 1 mm to 10 mm, or the like. The shape in the pattern of the adhesive 5 may be a circle, an ellipse, a gourd-like shape, a square, a rectangle, a drop-like shape or the like.

Note that, after the back sheet 3 is decomposed in water, coated region 50a and 50b, which are coated with the adhesive 5 (see FIGS. 4 and 5), might be connected to one another with the constituent fibers. To try to prevent this, in the back sheet 3, the width of a non-coated region 50c, which is not coated with the adhesive 5, is preferably greater than the length (fiber length) of the fibers forming the non-woven fabric used as the back sheet 3 (the sheet pieces 3A to 3C). In the present embodiment, directions of the fibers forming the non-woven fabric are arranged along the longitudinal direction of the absorbent article 1. It should be noted, however, the directions of the fibers forming the non-woven fabric are not necessarily arranged along the longitudinal direction of the absorbent article 1.

The coated regions 50a and 50b may be scattered at random all over the back sheet 3. Alternatively, the coated regions 50a and 50b may be regularly arranged in the longitudinal and/or width and/or oblique directions.

A pressure-sensitive adhesive or a thermal-sensitive adhesive may be used as the adhesive 5. Here, the pressure-sensitive adhesive is mainly based on a synthetic rubber such as a styrene-ethylene-butadiene-styrene block copolymer (SEBS), a styrene-butadiene-styrene block copolymer (SBS) or styrene-isoprene-styrene block copolymer (SIS), while the thermal-sensitive adhesive is mainly based on a synthetic rubber such as EVA. A biodegradable adhesive or a water-soluble adhesive may also be used as adhesive 5.

Note that, even when using any of the types of adhesive 5 described above, the back sheet 3 can be broken into pieces by the force of the flow of water entering through the non-coated region 50c with which the adhesive 5 is not coated.

The coated regions 50a and 50b are provided to continuously extend from one surface 3x of the back sheet 3 (sheet pieces 3A to 3C) to the other surface 3y.

Specifically, as shown in FIGS. 4 and 5, the coated regions 50a and 50b are provided to penetrate in the thickness direction from the surface 3x (one surface) of the back sheet 3 (the sheet pieces 3A to 3C) facing the waterproof paper 7 (the absorber 4 side) to the surface 3y (the other surface) of the back sheet 3 (the sheet pieces 3A to 3C) facing the peeling paper 6.

In other words, the coated regions 50a and 50b are formed to penetrate across: the surface 3x of the back sheet 3 (the sheet pieces 3A to 3C) that faces the waterproof paper 7 (the absorber 4 side); the inside of the back sheet 3 (the sheet pieces 3A to 3C); and the surface 3y of the back sheet 3 (the sheet pieces 3A to 3C) that faces the peeling paper 6. Note that, when the waterproof paper 7 is not provided, the coated regions 50a and 50b are formed to penetrate across: the surface 3x of the back sheet 3 that faces the absorber 4; the inside of the back sheet 3; and the surface 3y of the back sheet 3 that faces the peeling paper 6.

Here, the coated regions 50a and 50b are formed by causing the adhesive 5 to penetrate into gaps among the material pieces (into interfiber spaces in a non-woven fabric, for example) of the back sheet 3 (the sheet pieces 3A to 3C).

(Method of Manufacturing Absorbent Article According to a Second Embodiment)

Hereinafter, with reference to FIGS. 6 to 8, a method of manufacturing the absorbent article 1 according to this embodiment will be briefly described.

Figure 6:
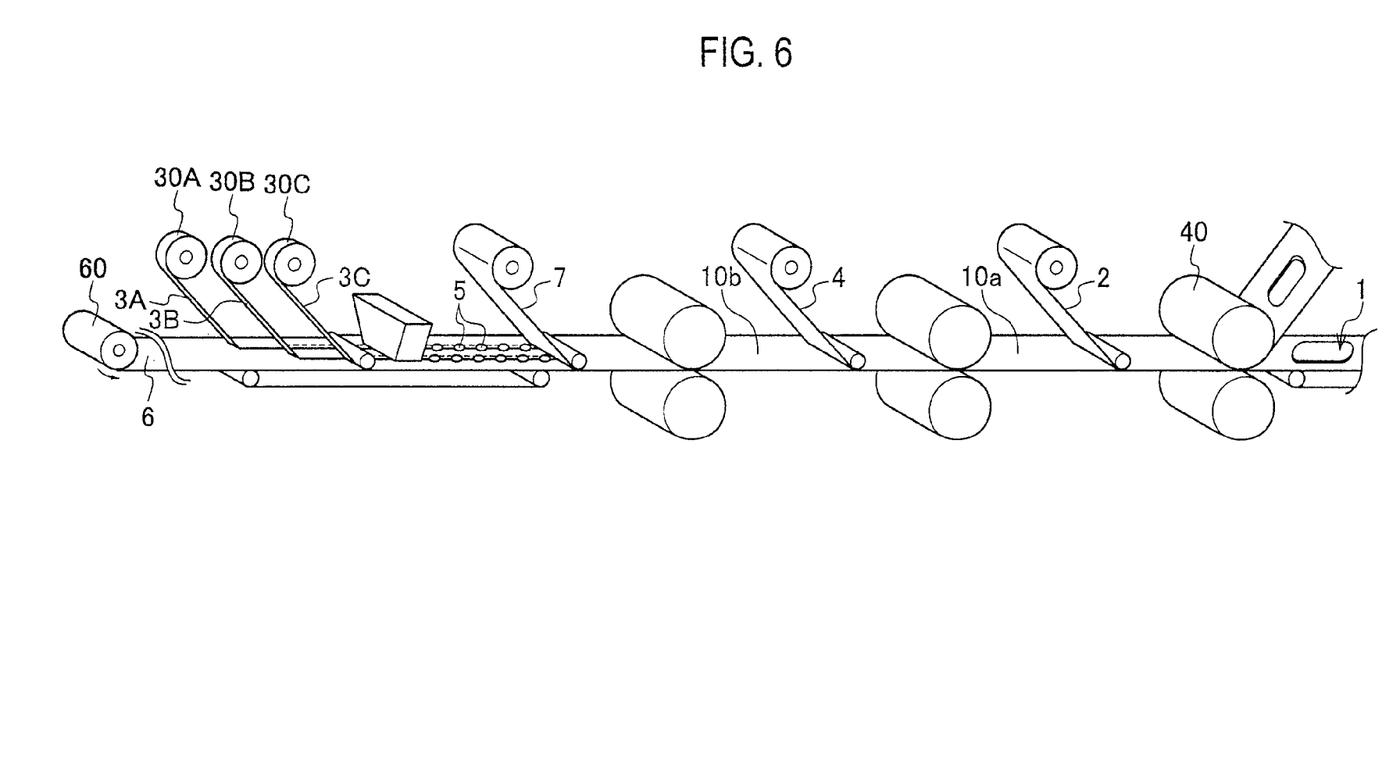
FIG. 6 is a diagram for illustrating an example of a method of manufacturing the absorbent article 1 according to the second embodiment of the present invention.

As shown in FIG. 6, firstly, continua of sheet pieces 3A to 3C are placed on a continuum of peeling paper sheets 6, while these continua are continuously conveyed on a line. Here, the continuum of peeling papers 6 is fed from a peeling paper roll 60, while the continua of sheet pieces 3A to 3C are fed respectively from multiple back-sheet rolls 30A to 30C.

Here, the multiple back-sheet rolls 30A to 30C are deployed along the moving direction of the line and the multiple back-sheet rolls 30A to 30C are arranged so that the continuum of sheet pieces 3A can partially overlap the continuum of sheet pieces 3B, and so that the continuum of sheet pieces 3B can partially overlap the continuum of sheet pieces 3C.

Figure 7:
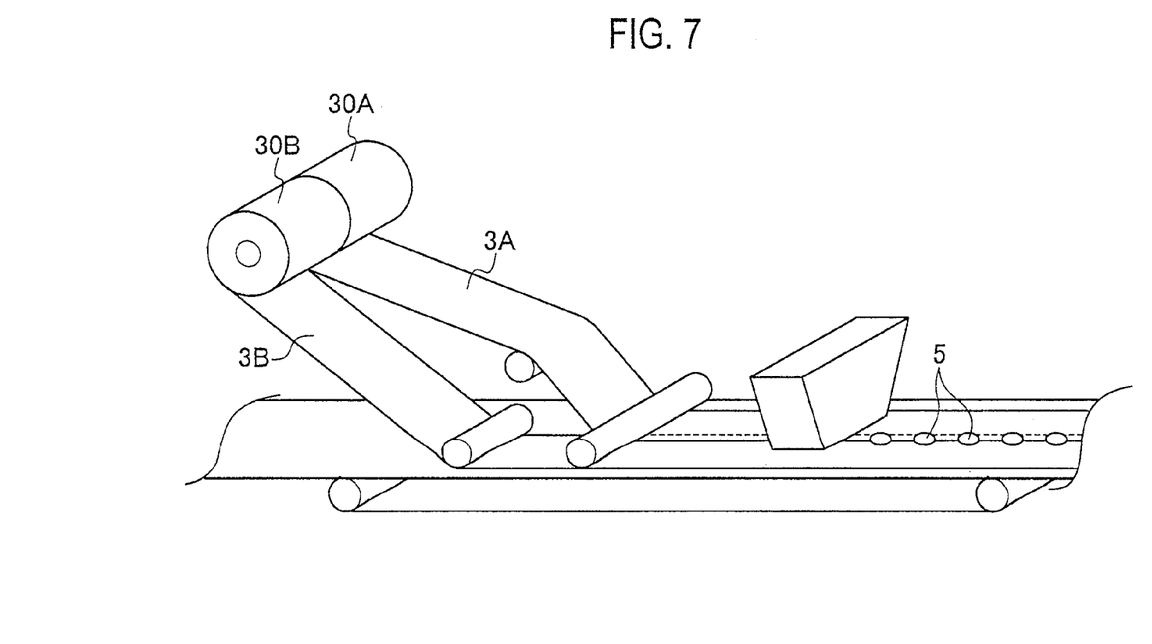
FIG. 7 is a diagram for illustrating another example of the method of manufacturing the absorbent article 1 according to the second embodiment of the present invention.

Alternatively, as shown in FIG. 7, a single back-sheet roll having one or more cuts may be prepared, and arranged so that a continuum of sheet pieces fed from the back-sheet roll can partially overlap each other to form one or more of the continua of sheet pieces.

Figure 8:
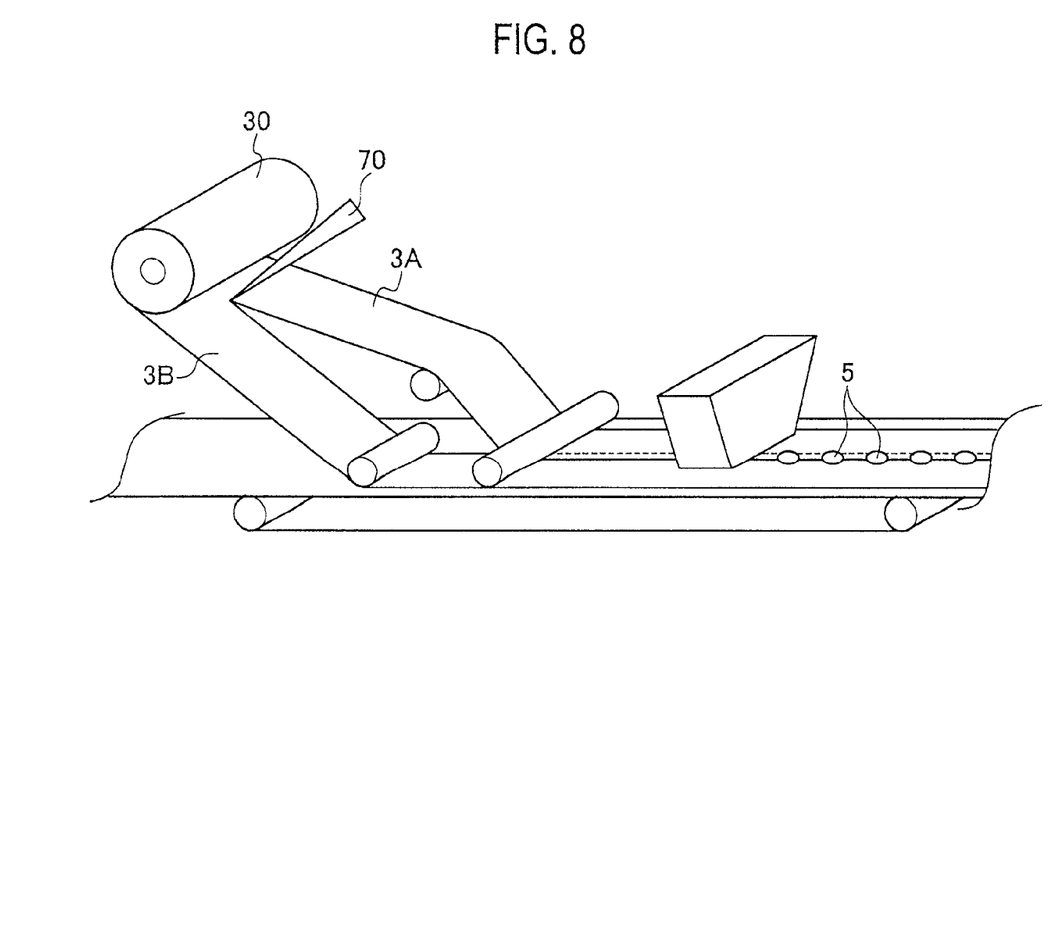
FIG. 8 is a diagram for illustrating still another example of the method of manufacturing the absorbent article 1 according to the second embodiment of the present invention.

Still alternatively, as shown in FIG. 8, a single back-sheet roll may be prepared to feed a continuum of sheet pieces to be cut by a cutter 70 into multiple continua of sheet pieces, and arranged so that each of these multiple continua of sheet pieces can partially overlap each other to form one or more of the continua of sheet pieces.

Secondly, the adhesive 5 is applied in a predetermined pattern described above to each overlapping regions 30x and 30y (see FIGS. 4 and 5) where adjacent two of the sheet pieces 3A to 3C overlap each other. Here, in the absorbent article 1 according to the first embodiment, the adhesive 5 is applied to be exposed only at the back side (the peeling paper 6 side) of the back sheet 3. On the other hand, in the absorbent article 1 according to the present embodiment, the adhesive 5 is applied to be exposed at the top and back sides of the overlapping regions 30x and 30y. With the adhesive 5, the sheet pieces 3A to 3C are joined together and the sheet pieces 3A to 3C are joined to the peeling paper 6.

Thirdly, a continuum of waterproof paper sheets 7 is placed on the continuum of back sheets 3, which is thus formed of the continua of sheet pieces 3A to 3C. The continuum of back sheets 3 are joined to the continuum of waterproof paper sheets 7 using the adhesive 5 exposed at the top side of the overlapping regions 30x and 30y.

Fourthly, an adhesive 10b is applied onto the continuum of waterproof paper 7, and then a continuum of absorber 4 is placed on the continuum of waterproof paper 7 and joined thereto.

Fifthly, an adhesive 10a is applied onto the continuum of absorber 4, and then a continuum of top sheets 2 is placed on the continuum of absorber 4 and joined thereto.

Sixthly, with a product cutter 40, the resultant continuum is cut into shapes each corresponding to the absorbent article 1.

In the absorbent article 1 according to the embodiment, the adhesive 5 is applied to the back sheet 3. Nevertheless, the absorbent article 1 can be dispersed at a higher speed in a drainage pipe or in a septic tank while having an improved fastening capability to an undergarment.

In the absorbent article 1, the back sheet 3 is formed of the multiple sheet pieces 3A to 3C. Accordingly, when the used absorbent article 1 is disposed of in a toilet, the adhesive 5 which joins the sheet pieces 3A to 3C together disintegrates in water, so that the back sheet 3, a single sheet formed of multiple sheet pieces connected together, is separated back into the multiple sheet pieces 3A to 3C. Thus, the sheet pieces 3A to 3C can be made of a material hardly decomposable in water.

In the absorbent article 1, the adhesive 5 which joins the sheet pieces 3A to 3C together is applied to be exposed at the top and back sides of the back sheet 3. Accordingly, the adhesive 5 can also be used to fasten the absorbent article 1 to an undergarment.

In the absorbent article 1, the adhesive 5 which joins the sheet pieces 3A to 3C together is applied in a pattern of shapes arranged at certain intervals. Accordingly, when the absorbent article 1 is put into water, water enters the inside thereof through the regions not coated with the adhesive 5, which facilitates separation of the sheet pieces 3A to 3C from one another caused by the flow of water.

In particular, the constituent fibers are previously cut at the peripheries of the sheet pieces 3A to 3C, and the coated region 50a and the non-coated region 50b, which are coated with the adhesive 5, are arranged at certain intervals. Accordingly, compared with a back sheet formed solely of a single sheet consisting of fibers entangled with one another, wherein the back sheet formed of a single sheet is broken as the fibers are untangled, the back sheet 3 can be broken at a higher speed than the back sheet formed of a single sheet.

In the absorbent article 1, the fibers forming non-woven fabric (the back sheet 3) are arranged to extend in the longitudinal direction of the absorbent article 1. In addition, each overlapping regions 30x and 30y where adjacent two of the sheet pieces 3A to 3C overlap each other is also arranged to extend in the longitudinal direction of the absorbent article 1. In other words, the back sheet 3 has no cut line extending in the width direction of the absorbent article 1. Accordingly, liquid that flows in the extending direction of the fibers is less likely to leak out of the absorbent article 1.

In the absorbent article 1, the adhesive 5 is applied so as to penetrate through the multiple sheet pieces 3A to 3C in the thickness direction of the absorbent article 1. Accordingly, the adhesive 5 can increase interlayer strength among the sheet pieces 3A to 3C by partially fixing the fibers in each of the sheet pieces 3A to 3C to the fibers in adjacent one of the sheet pieces 3A to 3C. In addition, this application of the adhesive 5 not only can prevent a phenomenon where part of the back sheet 3 and the adhesive 5 are left unpeeled from a wearer's undergarment when the absorbent article 1 is peeled off from the undergarment, but also makes the sheet pieces 3A to 3C less likely to separate from one another.

(Modification 1)

Hereinafter, an absorbent article 1 according to Modification 1 of the present invention will be described with reference to FIG. 9. The following description of the absorbent article 1 according to Modification 1 is focused on differences from the absorbent article 1 according to the embodiment of the present invention.

Figure 9:
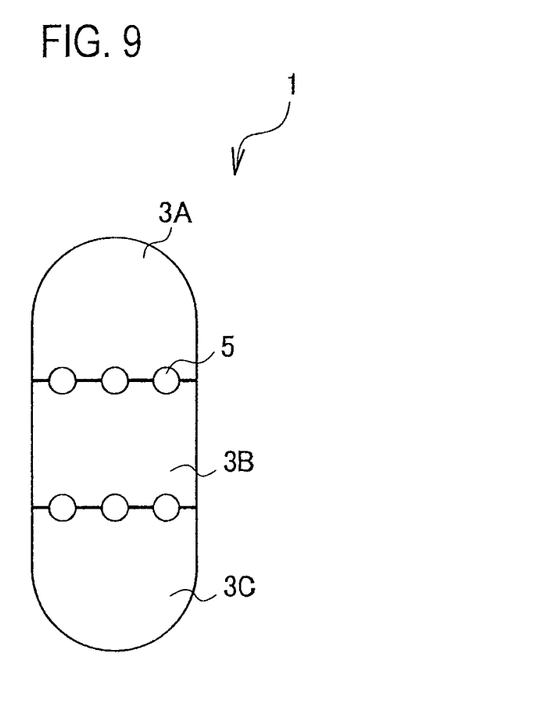
FIG. 9 is a plan view of a back sheet included in an absorbent article 1 according to Modification 1 of the present invention.

As shown in FIG. 9, in the absorbent article 1 according to Modification 1, each overlapping region where adjacent two of the sheet pieces 3A to 3C overlap each other is provided in the back sheet 3 so as to extend in the width direction of the absorbent article 1.

In the absorbent article 1 according to Modification 1, it is preferable to apply the adhesive 5 in a pattern designed to disperse a force applied to the absorbent article 1 when it is peeled off from a wearer's undergarment.

For example, such an application pattern of the adhesive 5, specifically an application pattern formed by multiple coated regions coated with the adhesive 5, should preferably be formed of rectangles arranged so that the shorter sides of the rectangles can extend perpendicular to the peeling directions of the absorbent article 1.

(Modification 2)

Hereinafter, an absorbent article 1 according to Modification 2 of the present invention will be described with reference to FIG. 10. The following description of the absorbent article 1 according to Modification 2 is focused on differences from the absorbent article 1 according to the embodiment of the present invention.

Figure 10:
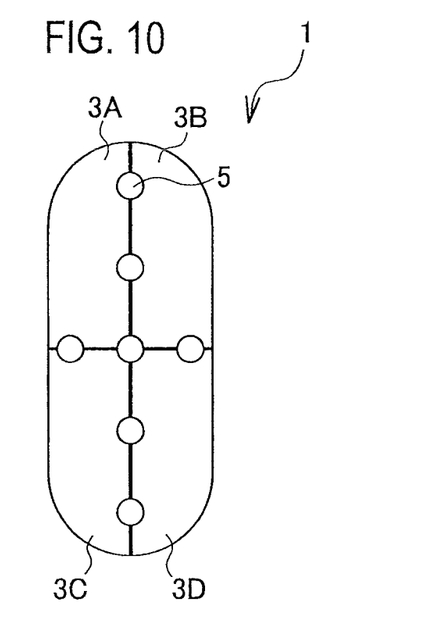
FIG. 10 is a plan view of a back sheet included in an absorbent article 1 according to Modification 2 of the present invention.

As shown in FIG. 10, in the absorbent article 1 according to Modification 2, the overlapping regions where adjacent two of the sheet pieces 3A to 3D overlap each other are provided in the back sheet 3 so as to extend both in the width and longitudinal directions of the absorbent article 1. Further, each lengths of the sheet pieces 3A to 3D is shorter than the length of the back sheet 3.

In the absorbent article 1 according to Modification 2, each of the sheet pieces 3A to 3D has the smallest size in length and width compared to the other embodiments shown in the figures and described herein. This provides the absorbent article 1 with improved dispersibility in water.

(Modification 3)

Hereinafter, an absorbent article 1 according to Modification 3 of the present invention will be described with reference to FIG. 11. The following description of the absorbent article 1 according to Modification 3 is focused on differences from the absorbent article 1 according to the embodiment of the present invention.

Figure 11:
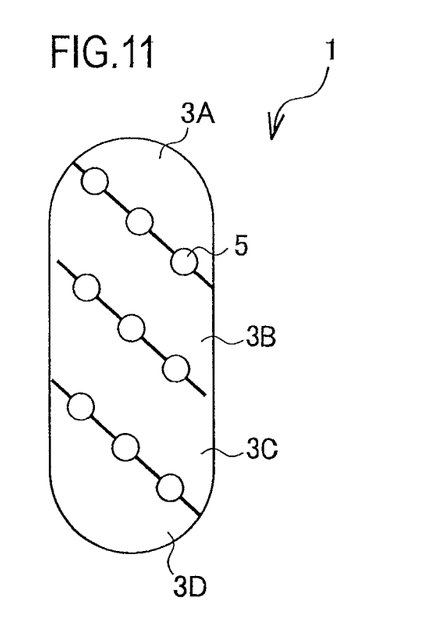
FIG. 11 is a plan view of a back sheet included in an absorbent article 1 according to Modification 3 of the present invention.

As shown in FIG. 11, in the absorbent article 1 according to Modification 3, each overlapping region where adjacent two of the sheet pieces 3A to 3C overlap each other is provided in the back sheet 3 so as to extend in a direction oblique to the longitudinal direction of the absorbent article 1 (at a 45° angle to the longitudinal direction, for example). Further, each lengths of the sheet pieces 3A to 3D is shorter than the length of the back sheet 3.

While the present invention has been described in detail above by using the foregoing embodiment, it should be apparent to those skilled in the art that the present invention is not limited to the embodiment described herein. The present invention may be practiced in the form of modifications and variations without departing from the basic concept and scope of the invention as defined in the appended claims. It is to be therefore understood that the disclosure herein is for purposes of illustration only and is not intended to limit the scope of the present invention.

Note that the entire content of Japanese Patent Application No. 2008-165153 (filed on Jun. 24, 2008) is incorporated by reference into this application.

Industrial Applicability

As described above, the present invention provides an absorbent article that has an improved fastening capability to an undergarment, and that is dispersible at a higher speed in a drainage pipe or in a septic tank, and to provide a method of manufacturing such an absorbent article.

The invention claimed is:

1. An absorbent article comprising:
a water-decomposable top sheet;
a water-decomposable back sheet; and
a water-decomposable absorber placed between the top sheet and the back sheet, wherein
the back sheet is formed of a plurality of sheet pieces each being smaller in size than a main body of the absorbent article, and each sheet piece at least partially overlaps with adjacent one or more of the other sheet pieces, and
an adhesive is applied to each overlapping region where adjacent two of the sheet pieces overlap each other.

2. The absorbent article according to claim 1, wherein the adhesive is discontinuously applied to the overlapping region.

3. The absorbent article according to claim 1, wherein the absorbent article is adapted to be bonded to an undergarment using the adhesive applied to the overlapping region.

4. The absorbent article according to claim 1, wherein the overlapping region is provided on the back sheet and is arranged to extend in a longitudinal direction of the absorbent article.

5. A method of manufacturing an absorbent article including:
a water-decomposable top sheet; a water-decomposable back sheet; and a water-decomposable absorber placed between the top sheet and the back sheet, the method of manufacturing an absorbent article comprising the steps of:
continuously conveying a plurality of continua of back sheets on a back sheet line;
placing the continua of back sheets to extend in a moving direction of the back sheet line so that each continuum of back sheets at least partially overlaps adjacent one or more of the other continua of back sheets; and applying an adhesive to each overlapping region where adjacent two of the continua of back sheets overlap each other.

* * * * *